United States Patent
Netsch et al.

(10) Patent No.: US 7,440,535 B2
(45) Date of Patent: Oct. 21, 2008

(54) CONE BEAM CT APPARATUS USING TRUNCATED PROJECTIONS AND A PREVIOUSLY ACQUIRED 3D CT IMAGE

(75) Inventors: Thomas Netsch, Hamburg (DE); Georg Rose, Duesseldorf (DE); Hermann Schomberg, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 90 days.

(21) Appl. No.: 11/568,115

(22) PCT Filed: Mar. 31, 2005

(86) PCT No.: PCT/IB2005/051087

§ 371 (c)(1),
(2), (4) Date: Oct. 20, 2006

(87) PCT Pub. No.: WO2005/104038

PCT Pub. Date: Nov. 3, 2005

(65) Prior Publication Data

US 2007/0195923 A1    Aug. 23, 2007

(30) Foreign Application Priority Data

Apr. 21, 2004   (EP) .................................. 04300216

(51) Int. Cl.
*G01N 23/00*   (2006.01)
(52) U.S. Cl. .......................................... 378/4; 378/901
(58) Field of Classification Search .................... 378/4, 378/901
See application file for complete search history.

(56) References Cited

U.S. PATENT DOCUMENTS

| | | | | |
|---|---|---|---|---|
| 4,550,371 A | * | 10/1985 | Glover et al. | 378/4 |
| 5,640,436 A | * | 6/1997 | Kawai et al. | 378/4 |
| 5,740,224 A | * | 4/1998 | Muller et al. | 378/11 |
| 5,951,475 A | | 9/1999 | Gueziec et al. | |
| 6,084,936 A | * | 7/2000 | Patch | 378/4 |
| 6,542,573 B2 | * | 4/2003 | Schomberg | 378/19 |
| 6,810,102 B2 | * | 10/2004 | Hsieh et al. | 378/4 |
| 6,856,666 B2 | * | 2/2005 | Lonn et al. | 378/8 |
| 7,254,259 B2 | * | 8/2007 | Hsieh et al. | 382/131 |
| 2004/0066911 A1 | | 4/2004 | Hsieh et al. | |

OTHER PUBLICATIONS

Bai, C., et al.; CT-based Attenuation Correction in PET Image Reconstruction for the Gemini System; 2004; IEEE Nuclear Science Symposium; vol. 5; pp. 3082-3086.

(Continued)

*Primary Examiner*—Edward J Glick
*Assistant Examiner*—Alexander H Taningco

(57) ABSTRACT

A 3D image of a region of an object is computed from truncated cone beam projection data acquired with an x-ray device and a prior CT image representing a larger region of the object. The truncated projection data are extrapolated to derive pseudoprojection data associated with projection directions outside the detector, and an intermediate CT image is reconstructed based on the truncated projection data completed with the pseudoprojection data. The prior CT image is then registered with the intermediate CT image. Forward projection data associated with projection directions outside the detector are computed from the truncated projection data and the registered prior CT image. The 3D image is finally reconstructed based on the truncated projection data completed with the forward projection data.

13 Claims, 2 Drawing Sheets

OTHER PUBLICATIONS

Figure 1:
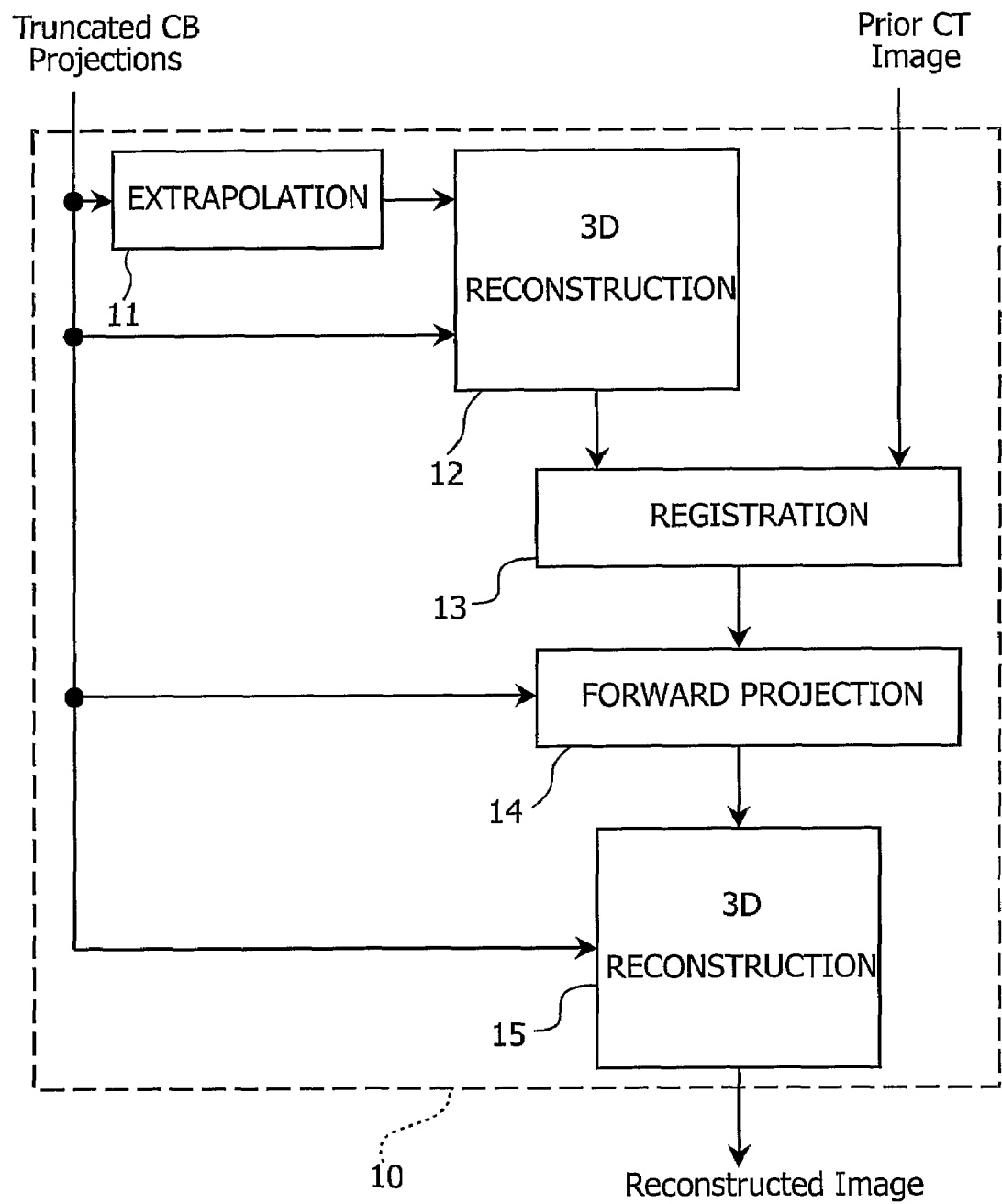

Defrise, M., et al.; A Cone-Beam Reconstruction Algorithm Using Shift-Variant Filtering and Cone-Beam Backprojection; 1994; IEEE Trans. on Medical Imaging; 13(1)186-195.

Feldkamp, L.A., et al.; Practical Cone-Beam Algorithm; 1984; J. Opt. Soc. Am.; 1(6)612-619.

Hsu, L., et al.; Automated Registration of CT and MR Brain Images Using 3-D Edge Detection; 1998; Proc. 20th An. Intl. Conf. IEEE Engineering in Medicine and Biology Society; 20(2)679-682.

Ramamurthi, K., et al.; Region of Interest Cone Beam Tomography with Prior CT Data; 2003; IEEE Asilomar Conf. on Signals, Systems & Computers; vol. 1; pp. 1924-1927.

Ramamurthi, K., et al.; Tomographic Reconstruction for Truncaded Cone Beam Data Using Prior CT Informaion; 2003; LNCS-MICCAI; 2879; 134-141.

* cited by examiner

CONE BEAM CT APPARATUS USING TRUNCATED PROJECTIONS AND A PREVIOUSLY ACQUIRED 3D CT IMAGE

The present invention relates to three-dimensional image processing, in particular in the field of 3D x-ray medical imaging.

In the context of the invention, the measurement apparatus is typically a C-arm system equipped with an image intensifier or a flat panel detector. A C-arm system is a common type of x-ray imaging device. It features an arm that is shaped like a "C" and carries an x-ray source, such as an x-ray tube, and an x-ray detector at its ends. The x-ray source has a small, point-like focal spot. When triggered, it emits a cone beam of x-rays towards the detector. The focal spot of the source corresponds to the apex of the cone.

A common type of detector is a combination of an x-ray image intensifier and a CCD camera. An image intensifier has a circular sensitive area, with a typical diameter of about 20 to 40 cm. The incoming x-ray photons are converted into an intermediate optical image that is read out by the CCD camera. The detector may also be a flat panel detector with a rectangular sensitive area, typically measuring from 20×20 to 40×40 cm2. The sensitive area of a flat panel detector is divided into a 2D array of small detector elements, which are read out directly. With both types of detectors, the final output of the detector is a 2D array of digital data that represents a sampled version of the spatial intensity distribution of x-ray photons that were impinging on the sensitive area of the detector when the measurement was made.

Together, the focal spot of the source and the sensitive area of the detector define a cone beam of x-rays. The cone beam may be narrowed by a shutter, or collimator. If there is an object between the source and the detector when the x-ray tube is on, one obtains a so-called cone beam projection of the object. Such a cone beam projection provides a 2D projection image of a 3D object and carries limited information about the spatial distribution of the x-ray attenuation coefficient within the object.

If the object is not fully illuminated by the cone beam, the projection is said to be truncated. The amount of truncation depends on the size of the detector, the size of the object, the projection direction, and other geometrical factors. If the object is a human body, measuring non-truncated cone beam projections requires an impracticably large detector. Thus, in medical applications, the measured cone beam projections are always truncated.

Within the limits imposed by the mechanical design of the C-arm system, the source may be moved to an arbitrary point on an isocentric sphere. This makes it possible to acquire cone beam projections from arbitrary directions of an object located at the isocenter. The source may also be moved in a continuous fashion along some trajectory confined to the mentioned isocentric sphere. This makes it possible to acquire a series of cone beam projections, with continuously varying directions, of an object located at the isocenter. If the movement involves only the rotation about a single axis, the resulting trajectory is an isocentric circular arc. By combining at least two rotational movements, non-planar source trajectories can be generated.

C-arm systems are widely used during interventional procedures, often in the so-called fluoroscopy mode. In this mode of operation, the C-arm system produces a time series of cone beam projections of the object to be imaged, possibly with varying projection directions. The resulting projection images assist the physician, e.g. for moving a catheter or placing a stent. In interventional procedures, it is often sufficient to project only a relatively small 3D region of interest (ROI). This can be done with a small detector, which is cheaper than a large detector. Also, a small detector allows the cone beam to be narrowed, thereby reducing the radiation dose delivered to the patient.

More recently, the use of C-arm systems has been suggested for true 3D imaging, or volume imaging. Volume imaging is achieved by first acquiring a series of cone beam projections of the object, where the source moves along some trajectory around the object, and then reconstructing the object from these projections, using a computer that executes a reconstruction algorithm.

The reconstructed image consists of a 3D array of volume elements, or voxels. It represents a discrete approximation to the spatial distribution of the x-ray attenuation coefficient within a 3D region of the object. The coordinates of the voxels with respect to a reference frame attached to the C-arm system are precisely known.

Given the acquisition geometry, as defined by the source trajectory and the shape of the cone beam, the region of projection (ROP) is defined as the volume contained in all the cone beams along the source trajectory. For example, if the source trajectory is a full circle and the sensitive area of the detector a disk, then the ROP is an isocentric sphere, whose diameter (typically from 15 to 25 cm) depends in part on the size of the detector. If the sensitive area of the detector is not a disk or the source trajectory not an isocentric full circle, the shape of the ROP is more complicated, but the ROP is still located at the isocenter, and its size is of the same order as in the preceding example.

Although an "exact" reconstruction of the contents of the ROP is often impossible (in medical applications), a fairly good reconstruction within the ROP may still be possible. This is because the missing portions of the cone beam projections provide only a small contribution to the exact result within the ROP. Moreover, the influence of the missing data decreases rapidly as the distance of the associated lines of integration from the ROP increases. Already a crude guess of the missing portions enables a satisfactory reconstruction within the ROP, and line integrals along lines that pass the ROP at a great distance can be safely ignored during the reconstruction process. Still, the source trajectory must be sensibly chosen. These observations suggest to extend the truncated projections so that they appear as non-truncated projections of an object somewhat bigger than the ROP and to feed the extended projections into one of the known reconstruction algorithms for non-truncated projections. The resulting image will differ from the true image only by some unknown, but weak and smoothly varying ghost image that does not clutter small anatomical details. The ghost image will be strongest near the boundary of the ROP and decrease rapidly towards the interior of this region. The less the projections are truncated and the more accurate the extended portions of the projections are, the better the reconstructed image will be.

A simple approach to extend the truncated projections is to make plausible assumptions about the shape of the object and the x-ray attenuation coefficient in it and to extrapolate the measured portions of the projections in accordance with these assumptions. Even the extremely simple assumption that the object is a ball or a cylinder with a constant x-ray attenuation coefficient in it works surprisingly well. If the underlying assumptions are grossly false, the result can be less satisfactory. In medical applications, this situation arises when the ROP is within a human brain. The ROP is then filled with soft tissue, but surrounded by bones which contribute significantly to the x-ray attenuation.

The type of volume imaging outlined hereabove is a form of cone beam computed tomography (CBCT). Strictly speaking, a C-arm gantry is not mandatory for the data acquisition. Other types of gantries might also be used. Source and detector might even be attached to, and moved by, robot arms. It is, however, desirable that the gantry be "open" so that the physician has free access to the patient. A C-arm gantry meets this demand.

C-arm-system-based CBCT provides a high, isotropic spatial resolution and is becoming a welcome adjunct to the standard fluoroscopy mode in interventional procedures. For example, in neuroradiology, the CBCT mode of operation may be used to verify the success of an intervention or aid the physician with decision-making during the intervention, should a complication arise. The patient can remain on the table and need not be moved to another scanner. The dose delivered to the patient is preferably as low as possible. For this reason, the ROP should be as small as possible. Besides, a small ROP can be realized with a small detector, which is cheaper than a large one.

The 3D distribution of the x-ray attenuation coefficient within the ROI of a patient may also be determined using a standard CT system with a rotating gantry. With older CT systems, the patient table, and with it the patient, is translated step by step along the long axis of the CT system. At each step, a 2D image of the "current" slice is reconstructed from a number of fan beam projections taken while the x-ray source rotates about the long axis of the system (patient). The problem of truncated fan beam projections does not arise (except, possibly, with obese patients). The resulting 2D images are finally stacked to form the desired 3D image. Newer CT systems use a continuous translation of the patient so that the source moves along a spiral around the patient. In any case, the voxels of the final 3D image are expressed in a reference frame attached to the CT system. The resolution of such a CT image is anisotropic and relatively poor along the long axis of the patient. A conventional CT gantry is "closed" and severely restricts the physician's access to the patient.

In neurological applications, a conventional 3D CT scan is routinely made hours or days before an intervention, for the purpose of diagnosis and planning. For the intervention itself, a C-arm system is used instead. As pointed out hereabove, the detector should then be relatively small, and a small detector may cause undesirable artifacts when the C-arm system operates in the CBCT mode.

In "Tomographic Reconstruction for Truncated Cone Beam Data Using Prior CT Information" (R. E. Ellis and T. M. Peters eds., MICCAI 2003, LNCS 2879, pp. 134-141, 2003), K. Ramamurthi and J. Prince propose to use a previously acquired 3D CT image for synthesizing the missing portions of the truncated cone beam projections acquired with the C-arm system. This amounts to numerically integrating the x-ray attenuation coefficient in the 3D CT image along the missing lines of integration that the C-arm system would have seen, if it had had a large detector. It is assumed that the previously acquired CT image is available in the reference frame of the C-arm system. In practice, this is not the case. The C-arm-system-based 3D CBCT image is not known a priori so that it cannot be used to register with the previously acquired CT image. The paper leaves it for further study to develop robust 2D-3D registration algorithms for that purpose, but this is a difficult task with the complex geometry of the cone beam projections and the fact that these projections do not cover the same information as the prior CT image.

An object of the present invention is to improve the quality of CBCT images obtained by means of a detector of relatively small lateral extension such as those used in some C-arm systems.

The invention thus proposes an apparatus for reconstructing 3D images as set out in claim 1. Preferred features of that apparatus are recited in claims 2-7. Another aspect of the invention relates to a computer program product as defined in claim 8 and dependent claims 9-13.

The invention takes advantage of an intermediate CBCT image, obtained by extending the available truncated cone beam projections using a simple extension method such as that alluded to above. The resulting image is not as good as the final image, but still good enough for registration purposes. Such registration can be performed in the 3D domain, preferably on the basis of local correlations between the intermediate image and the prior CT image. Once the registration has been completed, the missing portions of the truncated projections are synthesized using the prior 3D CT image.

A coarse sampling will often be sufficient in that synthesis, which speeds up the procedure. The missing portions are then up-sampled by interpolation, and the synthesized and interpolated data are used to complete the truncated cone beam projections for the second (final) reconstruction. The resulting CBCT image is almost free of truncation artifacts.

Figure 2:
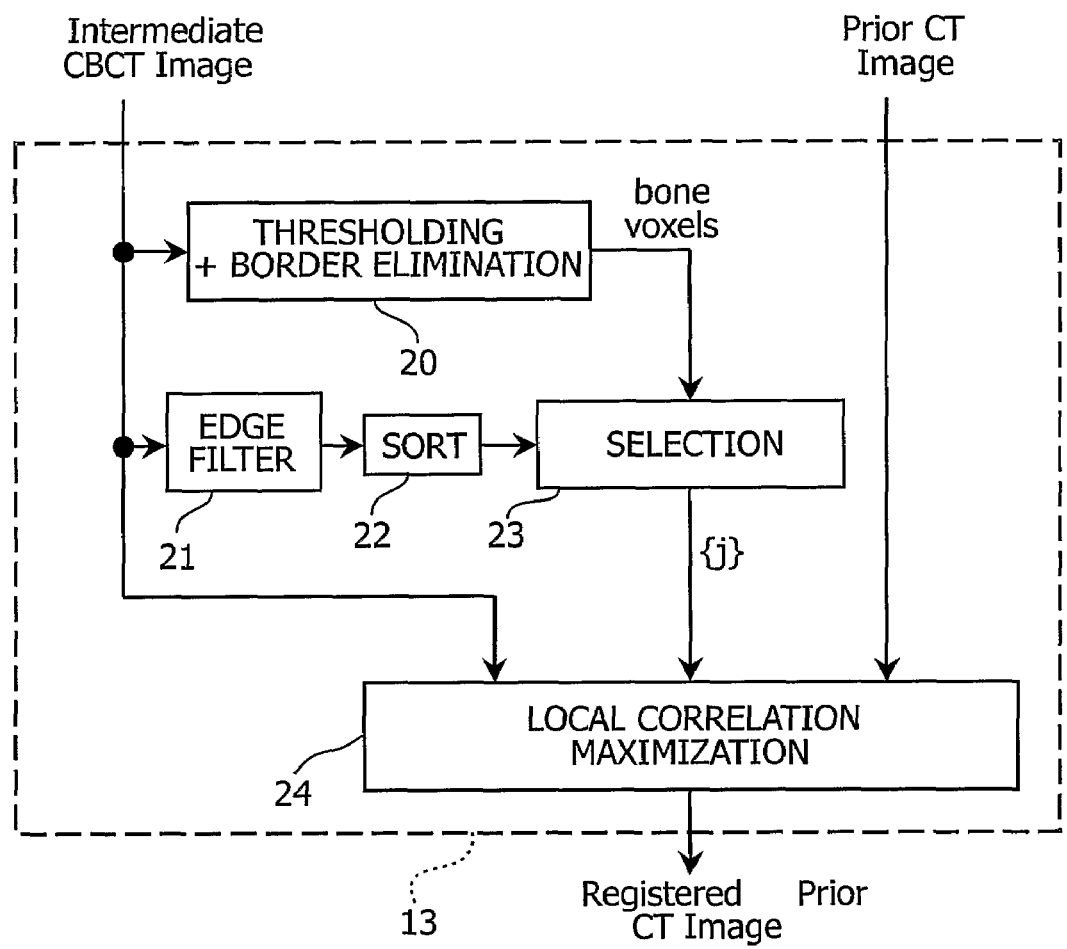

Other features and advantages of the invention will become apparent in the following description of non-limiting examples, with reference to the accompanying drawings, in which:

FIG. 1 is a block diagram of an apparatus in accordance with the invention; and FIG. 2 is a block diagram of a registration module of that apparatus.

FIG. 1 illustrates an image reconstruction apparatus usable to reconstruct 3D images from truncated cone beam (CB) projections which have been acquired by mean of a C-arm x-ray device having a relatively small detector. Therefore, the x-ray device has a relatively small region of projection (ROP), for example covering a region of interest (ROI) in an interventional procedure. Such small detector allows for a reduction of the radiation dose. It is also cheaper than a large detector.

The apparatus 10 has two inputs, one for receiving the truncated CB projections, along with data describing the acquisition geometry (C-arm layout, source trajectory, . . . ), and the other for receiving a previously computed CT image. The prior CT image may be an image of the whole object which is partly seen in the truncated CB projections. In such a case, the prior CT image is for example derived from cone beam projections previously acquired in a scan performed with a large detector. Alternatively, the prior CT image can cover only part of the object, provided that such part includes the ROP while being significantly larger than the ROP. For example, such prior CT image may be obtained as an output of the reconstruction apparatus 10 described herein.

The apparatus 10 is shown in a block diagram form FIG. 1. In a typical implementation, the modules 11-15 shown in FIG. 1 are software modules, i.e. consist of computer program code written to carry out the data processing steps described in detail below. The apparatus 10 then consists of a computing platform such as a workstation associated with the C-arm x-ray device used to acquire the truncated CB projections, with a memory where the prior CT image is stored, and with a display used to visualize slices of the reconstructed CBCT image. The computer program including data processing modules 11-15 may also be loaded to upgrade an existing workstation associated with a C-arm x-ray device. The modules 11-15 can also be implemented as hardware circuits.

In a first step of the reconstruction procedure, the extrapolation module 11 uses a simple extension method to extrapolate the line integrals outside the field of view of the detector. The extension method here can be a coarse one, such as the simple "radial" extension method disclosed in U.S. Pat. No. 6,542,573. Each row of each truncated projection is extended by fitting an elliptical arc to both of its ends. The lateral extent of the extension is controlled by an extension factor, which is the ratio of the lateral extent of the extended projections to the lateral extent of the truncated projections. Outside the detector, the extrapolated line integrals are referred to as pseudo-projection data.

An appropriate reconstruction algorithm, such as the one disclosed in in "A cone-beam reconstruction algorithm using shift-variant filtering and cone-beam back-projection", M. Defrise and R. Clack, IEEE Trans. Med. Imag., vol. 13, pp. 186-195, 1994, is then applied by the 3D reconstruction module 12 to the truncated CB projections completed with the pseudo-projection data. If the source trajectory is a circular arc, an even simpler "tangential" extension method is enough for module 12, such as the FDK algorithm disclosed in "Practical cone-beam algorithm", L. A. Feldkamp, L. C. Davis and W. J. Kress, J. Opt. Soc. Amer. A, vol. 1, pp. 612-619, 1984. The resulting intermediate CBCT image is expressed in the reference frame of the C-arm system.

The following step, carried out by module 13, consists in registering the prior CT image with the intermediate CBCT image of the ROP obtained in the previous step, using a suitable image registration algorithm. Such algorithms are able to handle different voxel and image sizes, as well as modest anatomical differences between the two images. This step yields the prior CT image expressed in the reference frame of the C-arm system.

Using the registered prior CT image output by module 13, the forward projection module 14 evaluates the missing line integrals of the x-ray attenuation coefficient that the C-arm system would have measured, if it had had a large detector.

Advantageously, module 14 performs an actual integration of the x-ray attenuation coefficient with a coarse spatial resolution, i.e. for only some of the pixels of the virtual detector represented by the real C-arm detector extended laterally with the same pixel resolution. For example the integration can be explicitly computed every four pixels, such as those of even row and column indices. If the number of projections is large, it may also be sufficient to carry out the integration only for every n-th projection, where n is a small positive integer, e.g. n=2. The coarse sampling saves computation time. Using interpolation, module 14 then estimates the line integrals that were not calculated explicitly. This is faster than calculating all of the missing data, and still accurate enough.

In addition, module 14 may apply a linear transformation to the forward projection data in order to match those data with the truncated CB data at the border of the detector. For example, a gain and an offset are calculated by means of a least square fit between the forward projection data and the truncated CB data in an overlap margin along the border. These parameters are useful to compensate for possibly differing beam qualities and scatter contributions in the different scans.

The measured truncated cone beam projections are completed with the forward projection data computed by module 14 to provide completed CB projections at the input of a second 3D reconstruction module 15. That module reconstructs a final 3D image of the ROP from the completed cone beam projections, using an appropriate reconstruction algorithm, such as the one disclosed in the above-mentioned paper of M. Defrise, et al. If the source trajectory is a circular arc, the FDK algorithm may be used instead. The resulting CBCT image is almost free of truncation artifacts.

Module 13 applies a rigid 3D image registration technique to match the prior CT image with the intermediate CBCT image. Intensity-based registration methods using similarity measures, such as cross-correlation or mutual information, are not readily applicable since the reference image and the intermediate image do not share the same anatomical information due to the truncation, in particular for bone structures. It is preferable to use a registration method based on the calculation of local correlation coefficients for a number of small neighborhoods in the intermediate CBCT image. The neighborhoods are selected in the vicinity of bones of the intermediate CBCT image, which are first determined by applying a threshold. Such a selection strategy has the advantage that the image similarity is only evaluated in areas providing related gray value information.

This 3D image registration technique is illustrated by the block diagram of the registration module 13 shown in FIG. 2. A thresholding module 20 segments the intermediate CBCT image by means of a fixed threshold to yield the voxels which presumably represent bones in the image. From the segmented image, module 20 may further remove all voxels situated outside a circle in each 2D-slice, such circle having a diameter defined as the minimum extension of the ROP in the x and y directions. The output of module 20 is a list of 3D coordinates of relevant bone voxels within the intermediate CBCT image.

Module 13 also includes a conventional edge filter 21, e.g. a Sobel or Canny filter, to which the intermediate CBCT image is applied. Filter 21 assigns to each voxel of the ROP an edge strength value corresponding to a maximum gradient of the x-ray attenuation coefficient in the 3D space or in 2D slices. A sorting module 22 sorts the voxels into a list ordered according to their edge strength values (largest value first). The voxels of the list are processed sequentially by a selection module 23 which, for each voxel i in the list, counts the number k(i) of bone voxels (as indicated by module 20) in some local neighborhood. Such neighborhood is for example a 7×7×7 cube centered on the voxel of the list which is being considered.

Module 23 builds a template which is made of voxels of the list having at least K bone voxels counted in their respective local neighborhoods. The integer K can be taken relatively small, e.g. K=3, in order to eliminate very small absorbing regions which are most probably not representative of bone structures. The template may consist of a fixed number N of voxels taken at the top of the list and satisfying the k(i)≧K criterion. Alternatively, the list is first screened to eliminate the voxels which do not satisfy the k(i)≧K criterion, and module 23 retains in the template the first Q% of the screened list (e.g. Q%=3%), thus yielding a variable number N of voxels in the template. The selection of a restricted number of template voxels at the top of the list ensures that these N voxels are representative of the most pronounced gray value transitions, and hence of the most probable bone contours present in the intermediate CBCT image.

In a subsequent step, the voxels of the template, denoted by the index j in FIG. 2, are used by module 24 as anchoring points to carry out the registration based on local correlation similarity. Module 24 determines a spatial transformation of the prior CT image which maximizes a local correlation measurement M(T), at the voxels of the template, between the intermediate CT image and the transformed prior CT image. Each, transformation tested in the optimization procedure is for instance defined by a set T of 6 parameters corresponding to a translation vector (3 coordinates) and to 3 rotation angles.

The local correlation measurement may be of the form:

$$M(T) = \frac{1}{N} \sum_j \frac{\left[\sum_{i \in n(j)} (b_i - \bar{b}_j)(t_i - \bar{t}_j)\right]^2}{\sum_{i \in n(j)} (b_i - \bar{b}_j)^2 \sum_{i \in n(j)} (t_i - \bar{t}_j)^2}$$

where the summation is made over the N voxels j of the template, n(j) denotes a local neighborhood of voxel j (e.g. the 5×5×5 cube centered on voxel j at the voxel resolution of the two images), bi is the x-ray attenuation value of voxel i of n(j) in the intermediate CT image, ti is the x-ray attenuation value of voxel i of n(j) in the prior CT image transformed by T, $\bar{b}_j$ and $\bar{t}_j$ are respectively the mean values of bi and ti within n(j).

Efficient algorithms usable by module 24 for maximizing M(T) are disclosed in "Towards real-time multi-modality 3D medical image registration", by T. Netsch et al., International Conference on Computer Vision (ICCV'01), Vancouver, BC, pages 501-508, 2001, to which reference may be made. The optimum set of parameters T constitutes registration data determined by module 24 and applied to the prior CT image to provide the registered image processed by the forward projection module 14.

Although the invention has been described with reference to preferred implementations thereof, it will be appreciated that various modifications can be made to those implementations without departing from the spirit and scope of the invention.

The invention claimed is:

1. An apparatus for reconstructing a 3D image of at least a first region of an object from truncated cone beam projection data acquired by means of an x-ray device having a source-detector assembly moved along an acquisition trajectory such that a cone beam between the source and the detector encompasses said first region, the apparatus comprising:
    extrapolation means for processing the truncated projection data to derive pseudo-projection data associated with projection directions outside the detector;
    first 3D reconstruction means for reconstructing an intermediate CT image covering at least the first region of the object based on the truncated projection data completed with the pseudo-projection data;
    registration means for computing registration data representing a spatial transformation selected to register a prior CT image, representing a second region of the object including the first region and larger than the first region, with the intermediate CT image;
    forward projection means for processing the truncated projection data and the registered prior CT image to derive forward projection data associated with projection directions outside the detector; and
    second 3D reconstruction means for synthesizing a reconstructed CT image covering at least the first region of the object based on the truncated projection data completed with the forward projection data.

2. The apparatus as claimed in claim 1, wherein the registration means comprise means for determining a template of voxels of the intermediate CT image which are representative of contours present in the intermediate CT image, and means for determining a spatial transformation of the prior CT image which maximizes a local correlation measurement, at the voxels of the template, between the intermediate CT image and the transformed prior CT image.

3. The apparatus as claimed in claim 2, wherein the means for determining the template comprise means for determining a set of voxels of the intermediate CT image having respective x-ray attenuation values above a threshold, and means for selecting the voids of the template whereby each void of the template has a respective local neighborhood including at least a predefined number of voxels of said set.

4. The apparatus as claimed in claim 3, wherein the means for selecting the voxels of the template are arranged to select voids of the intermediate CT image having maximum edge strength values among the voids having local neighborhoods including at least the predefined number of voids of said set.

5. The apparatus as claimed in claims 2, wherein the maximized local correlation measurement is of the form $$\frac{1}{N} \sum_j \frac{\left[\sum_{i \in n(j)} (b_i - \bar{b}_j)(t_i - \bar{t}_j)\right]^2}{\sum_{i \in n(j)} (b_i - \bar{b}_j)^2 \sum_{i \in n(j)} (t_i - \bar{t}_j)^2}$$

where N is the number of voxels of the template, j is a voxel index, n(j) denotes a neighborhood of voxel j, $b_i$ and $t_i$ are x-ray attenuation values of void i, within n(j) in the intermediate CT image and in the transformed prior CT image, respectively, and $b_j$ and $t_j$ are the mean values of the x-ray attenuation values within n(j) in the intermediate CT image and in the transformed prior CT image, respectively.

6. The apparatus as claimed in claim 1, wherein the forward projection means comprise first computing means for obtaining first forward projection data with a coarser resolution than the truncated cone beam projection data by means of the registered prior CT image, and second computing means for interpolating the first forward projection data to provide the forward projection data with the same spatial resolution as the truncated projection data.

7. The apparatus as claimed in any one of the preceding claims, wherein the forward projection means comprise linear transformation means to fit the forward projection data with the truncated cone beam projection data in a region located along the border of the detector.

8. A computer readable storage medium containing instructions which, when executed by a computer for reconstructing a 3D image of at least a first region of an object from truncated cone beam projection data acquired by means of an x-ray device having a source-detector assembly moved along an acquisition trajectory such that a cone beam between the source and the detector encompasses said first region, cause the computer to perform the step of:
    extrapolating the truncated projection data to derive pseudo-projection data associated with projection directions outside the detector;
    reconstructing an intermediate 3D CT image covering at least the first region of the object based on the truncated projection data completed with the pseudo-projection data;
    registering a prior CT image, representing a second region of the object including the first region and larger than the first region, with the intermediate CT image;
    processing the truncated projection data and the registered prior CT image to derive forward projection data associated with projection directions outside the detector; and synthesizing a reconstructed CT image covering at least the first region of the object based on the truncated projection data completed with the forward projection data.

9. The computer readable storage medium as claimed in claim 8, wherein the instructions for registering the prior CT image with the intermediate CT image comprise instructions for determining a template of voxels of the intermediate CT image which are representative of contours present in the intermediate CT image, and instructions for determining a spatial transformation of the prior CT image which maximizes a local correlation measurement, at the voxels of the template, between the intermediate CT image and the transformed prior CT image.

10. The computer readable storage medium as claimed in claim 9, wherein the instructions for determining the template comprise instructions for determining a set of voxels of the intermediate CT image having respective x-ray attenuation values above a threshold, and instructions for selecting the voxels of the template whereby each voxel of the template has a respective local neighborhood including at least a predefined number of voxels of said set.

11. The computer readable storage medium as claimed in claim 10, wherein the instructions for selecting the voxels of the template select voxels of the intermediate CT image having maximum edge strength values among the voxels having local neighborhoods including at least the predefined number of voxels of said set.

12. The computer readable storage medium as claimed in claim 8, wherein the instructions to derive forward projection data comprise instructions for obtaining first forward projection data with a coarser resolution than the truncated cone beam projection data by means of the registered prior CT image, and instructions for interpolating the first forward projection data to provide the forward projection data with the same spatial resolution as the truncated projection data.

13. The computer readable storage medium as claimed in claim 8, wherein the instructions to derive forward projection data comprise instructions to fit the forward projection data with the truncated cone beam projection data in a region located along the border of the detector.

* * * * *